United States Patent
Martinez et al.

(10) Patent No.: US 8,436,300 B2
(45) Date of Patent: May 7, 2013

(54) METHOD FOR CHARACTERISATION OF DIELECTRIC LAYERS BY ULTRAVIOLET PHOTO-EMISSION SPECTROSCOPY

(75) Inventors: Eugenie Martinez, Varces Allieres et Risset (FR); Cyril Guedj, Grenoble Cedex (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 147 days.

(21) Appl. No.: 13/063,059

(22) PCT Filed: Sep. 15, 2009

(86) PCT No.: PCT/EP2009/061897
§ 371 (c)(1),
(2), (4) Date: May 25, 2011

(87) PCT Pub. No.: WO2010/031748
PCT Pub. Date: Mar. 25, 2010

(65) Prior Publication Data
US 2011/0233398 A1    Sep. 29, 2011

(30) Foreign Application Priority Data
Sep. 17, 2008 (FR) ...................... 08 56242

(51) Int. Cl.
G01J 3/28 (2006.01)
(52) U.S. Cl.
USPC .......................................... 250/305
(58) Field of Classification Search .......... 250/305–397, 250/423 P
See application file for complete search history.

(56) References Cited

U.S. PATENT DOCUMENTS 5,695,628 A * 12/1997 Chiavarotti et al. .......... 205/340
7,420,163 B2 * 9/2008 Schueler ....................... 250/305

OTHER PUBLICATIONS

Diederich, L. et al., "Electron Affinity and Work Function of Differently Oriented and Doped Diamond Surfaces Determined by Photoelectron Spectroscopy", Surface Science, vol. 418, No. 1, pp. 219-239, XP-002527077, (Nov. 27, 1998).

Afanas'ev, V. V. et al., "Internal Photoemission at Interfaces of High-k Insulators With Semiconductors and Metals" Journal of Applied Physics, vol. 102, No. 25, pp. 081301-1-081301-28, XP-002527121, (Oct. 25, 2007).

Adamchuk, V. K. et al., "Internal Photoemission Spectroscopy of Semiconductor-Insulator Interfaces", Progress in Surface Science, vol. 41, No. 2, pp. 111-211, XP-024470022, (Oct. 1, 1992).

International Search Report Issued Jan. 22, 2010 in PCT/EP09/061897 filed Sep. 15, 2009.

* cited by examiner

Primary Examiner — Jack Berman
Assistant Examiner — Eliza Osenbaugh-Stewart
(74) Attorney, Agent, or Firm — Oblon, Spivak, McClelland, Maier & Neustadt, L.L.P.

(57) ABSTRACT

The electron affinity of thick dielectrics, of thickness greater than 10 nanometers, is measured by applying a polarization voltage varying between −4V and −40V, for example, and by taking several measuring points to determine a reference value of the photo-emission threshold ($E_S$), applying linear regression to an adjustment straight line (10) linking the measured thresholds (11) to the respective values of the square root of the voltage V.

3 Claims, 2 Drawing Sheets

METHOD FOR CHARACTERISATION OF DIELECTRIC LAYERS BY ULTRAVIOLET PHOTO-EMISSION SPECTROSCOPY

The subject of this invention is a method for characterisation of dielectric layers by ultraviolet photo-emission spectroscopy which, as will be seen, is of particular utility with thick dielectrics, typically of the order of 100 nanometers.

The electron affinity of high or low permittivity dielectrics is an important property to measure in the electronic industries, since it determines the level of the electrical leakage currents at the interfaces, and therefore the reliability of the components.

Measurements of this electron affinity can be made by ultraviolet photo-emission spectroscopy. The dielectric material is illuminated by ultraviolet rays, with an energy hv=20 à 50 eV, which ionises the atoms of the material. Electrons are then emitted from its surface, and their kinetic energy $E_c$ can be measured when they have been detected. It is possible to plot a spectrum of the emission intensity of the detected electrons as a function of their binding energy $E_L$, by applying the formula $E_L=hv-E_C$. The typical spectrum illustrated in FIG. 1 includes a peak 1 where the binding energy $E_L$ is highest, and which corresponds to the slowed secondary electrons in the material. The remainder of the spectrum has a shape somewhat like a plateau, and corresponds to the electrons of the material's valence band. The spectrum is limited by a photo-emission threshold $E_s$ on the side of peak 1, and by another threshold $E_v$ which defines the maximum level of occupation of the valence band. The electron affinity of the dielectric is then calculated by the relationship $qx=hv-E_g-E_s+E_v$, where $E_g$ is the gap of the material, presumed to be known, and which can be measured by the XPS, ellipsometric or REELS techniques. The word "gap" designates the energy interval separating the top of the valence band of a material from the bottom of its conduction band. $E_S$ and $E_V$ are in practice obtained by the intersection between linear adjustments of the adjacent parts of the spectrum and the horizontal axis of the diagram.

One difficulty of the method of characterisation concerns the accurate determination of the photo-emission threshold $E_S$, since it corresponds to the electrons the kinetic energy of which is zero. The electrons must transfer energy in order to release themselves from the material, enter into the spectrometer and be detected. It is impossible, therefore, to detect them without precautions. It is traditional to apply a direct electric polarisation voltage V to the sample subjected to measurement, so as to accelerate the electrons torn from its surface, and to give them sufficient additional energy to cross the spectrometer's surface potential barrier. This voltage applied to the sample may be between −4 V and −10 V. The threshold measured in the diagram is then equal to $E_S+|V|$, and all that need be done is to subtract from it the value, which is known since it was chosen by the operator, of the polarisation voltage V in order to obtain the value of the threshold $E_s$.

But this manner of proceeding is inapplicable with thick dielectrics, since their photo-emission threshold $E_s$ varies as a function of the polarisation voltage V applied to them, according, for example, to table 1 (for a porous SiOCH dielectric layer 100 nm thick). This threshold $E_s$ does not depend, or depends only slightly, on this polarisation voltage when the samples are thinner, 10 nm for example:

| V (V) | $E_s$ (eV) | $E_v$ (eV) |
|---|---|---|
| −5 | 20.5 | 3.9 |
| −10 | 22.9 | 4.0 |
| −15 | 24.9 | 4.0 |
| −20 | 26.7 | 4.1 |
| −25 | 28.3 | 4.0 |
| −40 | 32.5 | 4.2 |

The maximum threshold $E_v$ of the valence band, conversely, remains roughly uniform.

The purpose of the invention is to propose an improved method for characterisation of the photo-emission threshold of a thick dielectric, which corrects the influence of the polarisation voltage on the ultraviolet photo-emission spectrum of the dielectric, and which is able to provide a reference of this threshold, i.e. a reliable estimate for a zero polarisation voltage, despite the fact that direct measurement with this zero polarisation is impossible, as mentioned on page 2.

A general aspect of the invention is then a method for characterisation of a dielectric layer by ultraviolet photo-emission spectroscopy, including an electric polarisation of the layer subject to a direct current voltage and an irradiation of the layer by ultraviolet radiation. The measurement of the photo-emission threshold is repeated whilst varying the direct current voltage V over a range between −4V and −40 V for example, so as to establish electric fields of less than $10^7$ V/cm, depending on the thickness of the sample. A reference photo-emission threshold is calculated by a linear regression over a straight line grouping together the measured photo-emission thresholds according to the square root of the applied voltage V.

Indeed, the inventors have observed a linear correlation between the photo-emission threshold and the square root of the polarisation voltage through the sample, and with yet more confidence in respect of field values of below some $10^7$ V/cm, whereas this correlation no longer exists with the higher fields. The field effect created in the sample induces a quadratic reduction of the surface potential barrier with the increase of the absolute value of the applied voltage, which explains the observed correlation.

The invention will now be described with reference to the figures, of which:

FIG. 1, previously described, is an ultraviolet photo-emission spectrum,

Figure 2:
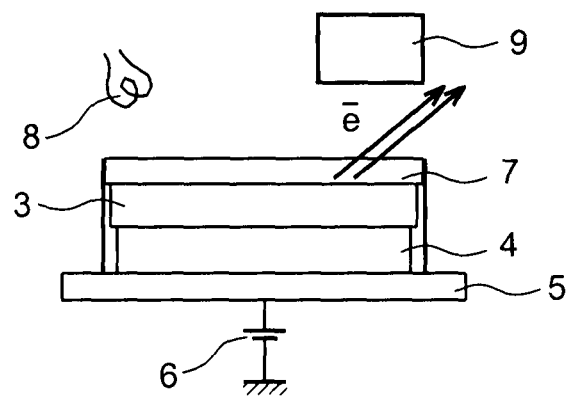
FIG. 2 illustrates a measuring device.

To begin with the description of FIG. 2. The measured sample includes a dielectric layer 3 on a support 4 which can be made from silicon. The support 4 is place on a sample-holder 5, to which a negative polarisation voltage is applied by a power source 6. A silver enamel bridge is made between the sample-holder 5 and the front face 7 of the sample from which the electrons are emitted. It covers the periphery of the dielectric layer 3 and the support 4. The device also includes an emitter 8 of ultraviolet light and a spectrometer 9. Other means of application of the polarisation, such as a parametric analyser, which also enables the currents induced in the sample to be measured, can be used. Detection is accomplished in a vacuum, with a pressure of less than $10^{-8}$ bar.

Figure 1:
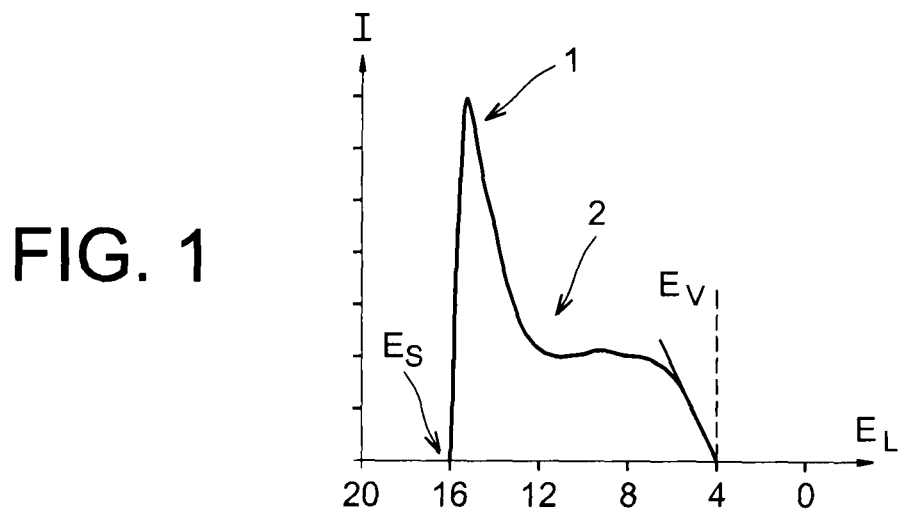
Figure 4:
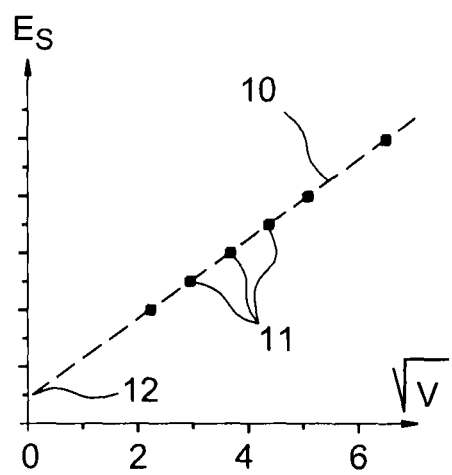
FIG. 4 is an illustration of results obtained.
Figure 3:
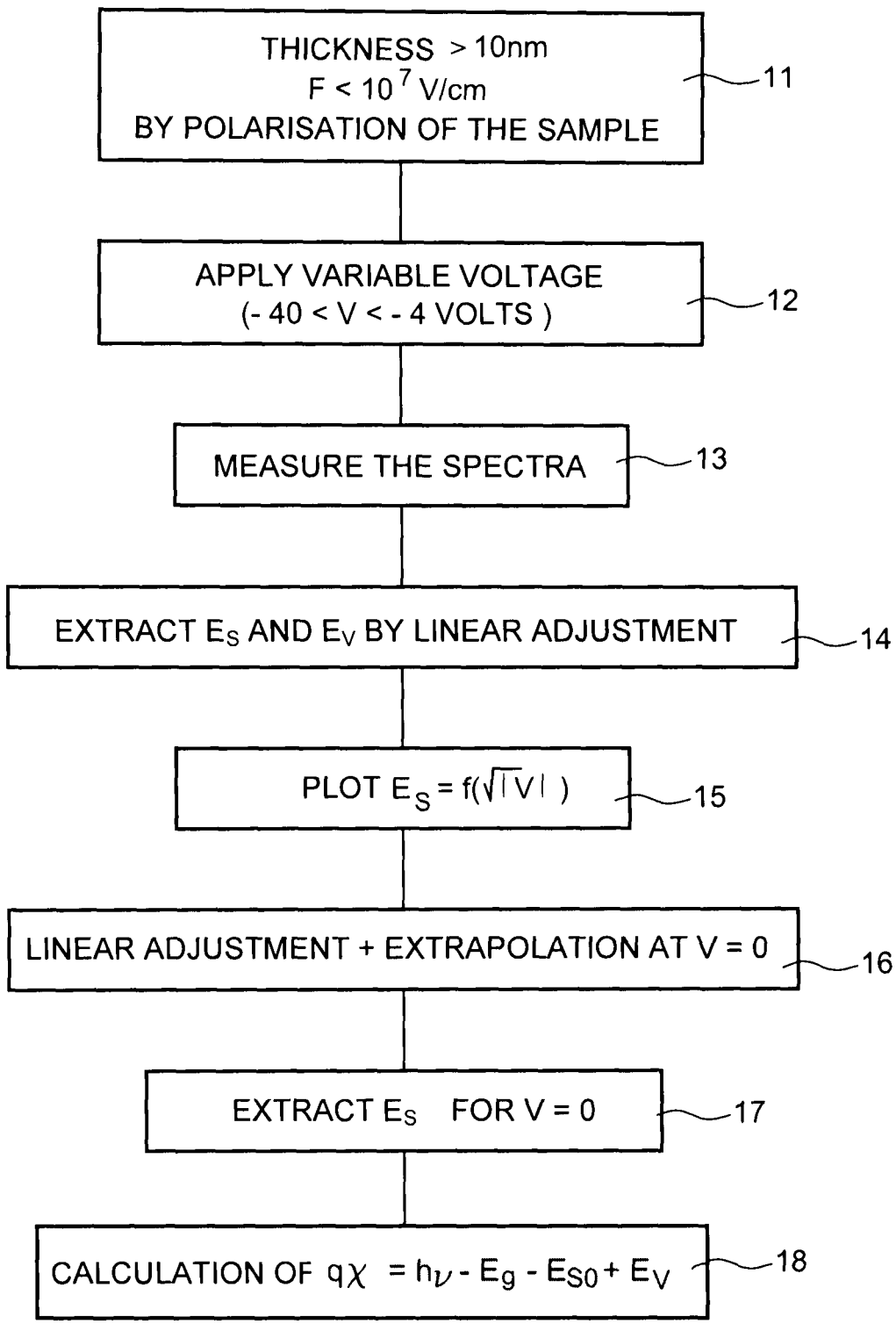
FIG. 3 is a flowchart.

A flowchart summarising the steps of measurement of the electron affinity is that of FIG. 3. In the case of a thick sample (of thickness equal to or greater than 10 nm, for example), an electric field of less than $10^7$ V/cm is created by polarisation of the sample according to step 11. A variable polarisation voltage, of between, for example, −4 and −40 V, is applied in step 12. For each of the voltage values the corresponding spectrum is measured in step 13. The emission threshold $E_s$ is extracted for each of these spectra, as is the opposing threshold $E_v$ in step 14. Linear adjustment is applied, calculating the intersections of the tangents to the spectrum with the horizontal axis, as was mentioned in connection with FIG. 1. The different values of the emission threshold are plotted as a function of the square root of the applied polarisation voltage V. The resulting straight line is determined by linear adjustment in step 15. It is represented in FIG. 4 as reference 10, where the measuring points have the reference 11. It is then possible to extrapolate the threshold value which would correspond to a zero polarisation voltage (point 12 of function 10) by a linear regression according to steps 16 and 17.

Finally, the electron affinity can be calculated in step 18 using the formula set out above.

A traditional method can be applied for thicknesses of dielectric of less than 10 nm, by application of a voltage which can be −5 V (corresponding to a field greater than $5 \cdot 10^6$ V/cm): the spectrum is measured; the thresholds $E_S$ and $E_V$ are deducted by linear adjustment and the electron affinity is calculated in the same way as in step 18.

The invention claimed is:

1. A method for characterisation of a dielectric layer by ultraviolet photo-emission spectroscopy, including an electric polarisation of the layer subject to a direct current voltage (V) and an irradiation of the layer by an ultraviolet radiation, a measurement of a photo-emission threshold corresponding to a maximum binding energy of electrons emitted by the layer, wherein the measurement is repeated whilst varying the direct current voltage so as to establish fields of less than $10^7$ V/cm through the layer, the photo-emission threshold is measured for each value of the applied voltage and the photo-emission threshold at zero voltage is calculated by regression over a straight line grouping together the photo-emission thresholds measured according to the square root of the voltage.

2. A method for characterisation according to claim 1, wherein the layer is of a thickness greater than or equal to 10 nm.

3. A method for characterisation according to claim 1, wherein the method also includes a step of calculation of an electron affinity of the layer.

* * * * *